United States Patent
Lange

(10) Patent No.: US 9,412,006 B1
(45) Date of Patent: Aug. 9, 2016

(54) CONTINUOUS TISSUE ANALYSIS SCORING SCHEME BASED ON CELL CLASSIFICATIONS

(71) Applicant: FLAGSHIP BIOSCIENCES, INC., Westminister, CO (US)

(72) Inventor: Holger Lange, Enger (DE)

(73) Assignee: FLAGSHIP BIOSCIENCES, INC., Westminister, CO (US)

(*) Notice: Subject to any disclaimer, the term of this patent is extended or adjusted under 35 U.S.C. 154(b) by 0 days.

(21) Appl. No.: 14/189,757

(22) Filed: Feb. 25, 2014

Related U.S. Application Data

(60) Provisional application No. 61/769,087, filed on Feb. 25, 2013.

(51) Int. Cl.
G06K 9/00 (2006.01)

(52) U.S. Cl.
CPC .................................. G06K 9/00147 (2013.01)

(58) Field of Classification Search
None
See application file for complete search history.

(56) References Cited

U.S. PATENT DOCUMENTS

| | | | | |
|---|---|---|---|---|
| 5,828,776 | A * | 10/1998 | Lee et al. | 382/133 |
| 8,311,276 | B2 * | 11/2012 | Kizuki et al. | 382/103 |
| 2006/0039593 | A1 * | 2/2006 | Sammak et al. | 382/133 |
| 2006/0188140 | A1 * | 8/2006 | Gholap et al. | 382/133 |
| 2009/0286695 | A1 * | 11/2009 | Cainarca et al. | 506/10 |
| 2010/0111396 | A1 * | 5/2010 | Boucheron | 382/133 |
| 2011/0090500 | A1 * | 4/2011 | Hu et al. | 356/337 |
| 2012/0076390 | A1 * | 3/2012 | Potts et al. | 382/133 |
| 2012/0243755 | A1 * | 9/2012 | Kaufman | 382/128 |
| 2012/0309030 | A1 * | 12/2012 | McKenna et al. | 435/7.24 |
| 2013/0064441 | A1 * | 3/2013 | Kask | 382/133 |
| 2015/0004630 | A1 * | 1/2015 | Lange et al. | 435/7.21 |

OTHER PUBLICATIONS

Wolff et al., "American Society of Clinical Oncology/College of American Pathologists Guideline Recommendations for Human Epidermal Growth Factor Receptor 2 Testing in Breast Cancer", Journal of Clinical Oncology, Jan. 1, 2007, vol. 25, No. 1, pp. 118-145.

* cited by examiner

*Primary Examiner* — Tahmina Ansari
(74) *Attorney, Agent, or Firm* — Coastal Patent Law Group, P.C.

(57) ABSTRACT

A method for a continuous scoring scheme used for the assessment of biomarker expressions in the analysis of tissue sections, and digital images thereof, is based on cell classifications.

20 Claims, 4 Drawing Sheets

Cells with Cell Classification

| P(0) | P(1+) | P(2+) | P(3+) | ICP(1+) | ICP(2+) | ICP(3+) | HER2 Score |
|---|---|---|---|---|---|---|---|
| 100% | 0% | 0% | 0% | 0% | 0% | 0% | 0.000 |
| 99% | 1% | 0% | 0% | 1% | 0% | 0% | 0.050 |
| 95% | 5% | 0% | 0% | 5% | 0% | 0% | 0.250 |
| 91% | 9% | 0% | 0% | 9% | 0% | 0% | 0.450 |
| 90% | 10% | 0% | 0% | 10% | 0% | 0% | 0.500 |
| 50% | 50% | 0% | 0% | 50% | 0% | 0% | 0.722 |
| 0% | 100% | 0% | 0% | 100% | 0% | 0% | 1.000 |
| 90% | 9% | 1% | 0% | 10% | 1% | 0% | 0.600 |
| 90% | 5% | 5% | 0% | 10% | 5% | 0% | 1.000 |
| 90% | 1% | 9% | 0% | 10% | 9% | 0% | 1.400 |
| 90% | 0% | 10% | 0% | 10% | 10% | 0% | 1.500 |
| 0% | 0% | 100% | 0% | 100% | 100% | 0% | 2.000 |
| 70% | 0% | 0% | 30% | 30% | 30% | 30% | 2.500 |
| 0% | 0% | 0% | 100% | 100% | 100% | 100% | 3.000 |

*FIG. 3*

CONTINUOUS TISSUE ANALYSIS SCORING SCHEME BASED ON CELL CLASSIFICATIONS

CROSS-REFERENCE TO RELATED APPLICATIONS

This application claims benefit of priority with U.S. Ser. No. 61/769,087, filed Feb. 25, 2013; the contents of which are hereby incorporated by reference.

BACKGROUND OF THE INVENTION

1. Field of the Invention

This invention generally relates to medical imaging; and more particularly, to the analysis of microscopic images from tissue sections.

2. Description of the Related Art

As before in radiology, now with the digitization of pathology, more precisely the imaging of histology slides, new computer-assisted methods can be used that go far beyond the ability of a human evaluation and interpretation of a tissue section using an optical microscope.

The scoring and interpretation schemes today have been designed for human evaluation and interpretation, and are therefore limited in complexity and required precision. Pathologists use mostly qualitative, but also semi-quantitative and quantitative assessments of single biomarker expressions in tissue sections.

One type of a quantitative scoring scheme is based on a classification of the cells into four ranked categories: 0, 1+, 2+ and 3+. The cells are counted per cell classification category and a discrete ranked score is determined by applying thresholds to the percentages of cells for those four cell classification categories.

Although useful, this type of scoring is limited when taking into consideration computerized systems and their abilities for acquisition of tissue analysis data.

The IHC HER2 scoring scheme described in Wolff et. al. (See References) is an example of such a quantitative scoring scheme. Cells are classified into the categories: 0, 1+, 2+ and 3+ based on the combination of two cell features, membrane staining intensity and membrane completeness, according to Table 1.

TABLE 1

| Cell Classification | Membrane Staining Intensity | Membrane Completeness |
|---|---|---|
| 0 | Negative | NA |
| 1+ | Weak Positive | Partial |
| 2+ | Medium Positive | Complete |
| 3+ | Strong Positive | Complete |

The cells are counted per cell classification category N(c), as expressed in Eq. 1.

$$N(c) = \sum^{Cells} \text{Classification(Cell)} = c; c \square \{0, 1+, 2+, 3+\} \quad \text{Eq. 1}$$

The inverse cumulative percentages ICP(c) for 3+ cells, 3+ and 2+ cells and 3+, 2+ and 1+ cells are calculated, as expressed in Eq. 2. Note that "inverse" stands here for the fact that the percentages are cumulated from high to low ranked categories, as opposed to the standard way from low to high.

$$ICP(c) = \sum_{i=c}^{3+} P(i); c \square \{1+, 2+, 3+\} \text{ with} \quad \text{Eq. 2}$$

$$P(i) = \frac{N(i)}{N} \text{ and } N = \sum_{i=0}^{3+} N(i)$$

Thresholds T(c) of 10%, 10% and 30% are defined corresponding to the inverse cumulative percentages ICP(c). The scores S(c) are defined as 0, 1+, 2+ and 3+ and are associated with the satisfaction of the threshold criteria ICP(c)≥T(c), as expressed in Eq. 3. Note that in the case of the IHC HER2 scoring scheme, the cell classification categories and the scores use the same ranked categories.

$$\text{Score} = \max\{S(0), S(c) \times [ICP(c) \geq T(c)]; c\square\{1+,2+,3+\}\} \quad \text{Eq.3:}$$

with S(0)=0
with S(1+)=1+ and T(1+)=10%
with S(2+)=2+ and T(2+)=10%
with S(3+)=3+ and T(3+)=30%

FIGS. 1(A-C) illustrate an example of the IHC HER2 scoring scheme. FIG. 1A illustrates the cells (circles) in an image of a tissue section, which are color-coded according to their classification (0—blue, 1+—yellow, 2+—orange and 3+—red). FIG. 1B shows the percentages of cells for the ranked cell classification categories. FIG. 1C shows the inverse cumulative percentages for the ranked cell classification categories. The thresholds T(1+)=10%, T(2+)=10% and T(3+)=30% (red) that apply to the corresponding inverse cumulative percentages ICP(1+), ICP(2+) and ICP(3+) (black) are shown as bold lines in the different cell classification categories. In this example, the highest cell classification category, where the inverse cumulative percentage is equal to or higher than the threshold, is 2+, illustrated by the green arrow. The score, corresponding to the cell classification category 2+, is 2+.

Discrete scores, like the one provided by the IHC HER2 scoring scheme, provide a classification into clinically-relevant categories, but make it hard to identify borderline cases and to provide a more precise and accurate assessment. While discrete scoring schemes seem to be appropriate for a subjective human evaluation and interpretation, sophisticated image analysis programs that objectively detect the cells on entire tissue sections and quantify the expression of biomarkers can leverage the use of continuous scoring schemes to provide more precise and accurate assessments.

Another limitation of existing scoring schemes designed for human evaluation and interpretation is the complexity of the cell classification. The IHC HER2 scoring scheme exhibits an already rather complex cell classification schemes, as it evaluates two cell features, which are still apparently related to the expression of a single biomarker. Using sophisticated image analysis programs that allow characterizing multiple cell features at the same time enables the use of more complex cell classification schemes based on multiple cell features to provide more precise and accurate assessments.

Continuous scoring schemes can be developed by expansion of already well-known and discrete scoring schemes that are based on cell classifications. New scoring schemes can be devised that rely on complex cell classification schemes incorporating multiple cell features.

Ultimately a pathologist can use computer-assisted scoring as an aid in their evaluation and interpretation of biomarker expressions in tissue sections.

SUMMARY OF THE INVENTION

In accordance with the invention, the lack of precision and accuracy of existing discrete scoring schemes for the assessment of biomarker expressions in tissue sections can be overcome by using continuous scoring schemes based on cell classifications, in particular when sophisticated image analysis programs are used to detect and characterize the cells and to quantify the biomarker expressions. The invention can be used to extend existing discrete scoring schemes to continuous scoring schemes. The invention can also be used to create new continuous scoring schemes. Using the cell classification as the basis for the scoring scheme provides a simple abstraction from the cell features. It enables the use of complex cell classification schemes based on multiple cell features in the scoring scheme.

These and other features and advantages of this invention are described in, or are apparent from, the following detailed description of the preferred embodiments.

BRIEF DESCRIPTION OF THE DRAWINGS

The preferred embodiments of this invention will be described, with reference to the following figures, wherein:

FIG. 3 shows a few different cell distributions with the corresponding continuous HER2 scores.

DETAILED DESCRIPTION OF THE PREFERRED EMBODIMENTS

Figure 1A:
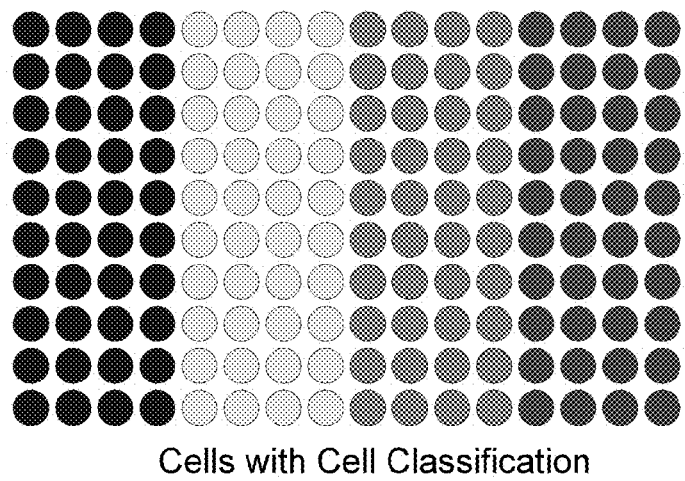
FIG. 1A illustrates cells in an image of a tissue section, which are color-coded according to their classification (0—blue, 1+—yellow, 2+—orange and 3+—red).

A key aspect to creating a continuous scoring scheme is to use or create a discrete scoring scheme and to provide a formula that provides the continuous values between the discrete scores.

One type of a discrete scoring scheme is based on a classification of the cells into a number of ranked categories. The cells are counted per cell classification category and a discrete ranked score is determined by applying thresholds to the percentages of cells in those cell classification categories.

The cell classification can be based on a single cell feature (e.g. nuclei staining intensity) or multiple cell features (e.g. membrane staining intensity and membrane completeness) depending on the application. Sophisticated image analysis programs allow characterizing multiple cell features at the same time and even to multiplex cell features across different tissue sections. Any of those cell features, including a characterization of the cell morphology, cell neighborhood, which includes a characterization of the tissue morphology, and the expression of multiple biomarkers, which can include different types of expressions (e.g. protein, gene and mRNA) using different acquisition systems (e.g. brightfield or fluorescence) or just different expressions (e.g. HER2, ER and PR), can be included in a computer-assisted scoring scheme.

Any cell classification scheme that allows mapping one or multiple cell features to discrete ranked categories can be used with this method. Computer-assisted scoring schemes can use machine-learning techniques to create cell classifiers that can be based on any number of cell features.

The cell classification categories can be defined, depending on the application, from coarse, like the classic cell classification into 0, 1+, 2+ and 3+, to fine, like defining a sampling of the measurements into separate categories (e.g. 0, 1, 2, 3, ... 255 for 8-bit precision). Without loss of generality, the cell classification categories can be defined as 0, 1, 2, 3, ... C−1, with C being the number of categories.

The cells are counted per classification category N(c), as expressed in Eq. 4.

$$N(c) = \sum_{}^{Cells} \text{Classification(Cell)} = c; \quad c \in \{0, 1, 2, \ldots C-1\} \qquad \text{Eq. 4}$$

The inverse cumulative percentages ICP(c) are calculated, as expressed in Eq. 5.

$$ICP(c) = \sum_{i=c}^{C-1} P(i); \, c \in \{1, 2, \ldots C-1\} \text{ with} \qquad \text{Eq. 5}$$

$$P(i) = \frac{N(i)}{N} \text{ and } N = \sum_{i=0}^{C-1} N(i)$$

Thresholds T(c) need to be defined (TBD—to be determined), depending on the application, corresponding to the inverse cumulative percentages ICP(c). Discrete ranked scores S(c) associated with the satisfaction of the threshold criteria ICP(c)≥T(c) need to be defined, depending on the application, as expressed in Eq. 6.

$$\text{Score}_{discreet} = \max\{S(0), S(c) \times [ICP(c) \geq T(c)]; c \in \{1, 2, \ldots C-1\}\} \qquad \text{Eq. 6:}$$

with S(0)=TBD
with S(c)=TBD and T(c)=TBD %

A formula to provide a continuous scoring for this type of discrete scoring schemes can be based on a function of different criteria, including the confidence into the actual score and the distance to the next higher score.

A function that can be used to combine the criteria is the maximum function (max), whereby the output of the criteria should already be mapped to the corresponding continuous scoring intervals. The choice of the maximum function would be consistent with how the discrete scores are calculated, as the maximum score that satisfies the different threshold criteria.

The mapping of the criteria can be done relative to the discrete scores using the half point between the actual score and the next lower score as the anchor to define the mapping intervals corresponding to the different discrete scores. Consequently, the maximum range for the mapping interval would be from the half point between the actual score and the next lower score to the half point between the actual score and the next higher score. Note that when using consecutive numbers for the discrete ranked scores, the rounding of the continuous score will provide the discrete score.

The confidence into the actual score can be measured by the difference between the actual percentage of cells ICP(k) and the required percentage of cells to pass the actual threshold T(k) for the actual score S(k). Intuitively, this provides a measure of confidence by how much the actual threshold was passed. If the actual percentage of cells just barely passed the threshold, the continuous score should be close to the border to the next lower score (e.g. 1.5 if the discrete score is 2 and the next lower discrete score is 1). If 100% of the cells passed the threshold, the continuous score should be a full score (e.g. 2.0). The calculation of the confidence into the actual score using a linear mapping and a linear normalization to the maximum range based on the outlined intuition is shown in Eq. 7. k is the index that corresponds to the actual discrete score. How k is calculated can be seen in Eq. 10.

$$\text{Confidence}(k) = (S(k) - S(k-1)) \times \frac{ICP(k) - T(k)}{100\% - T(k)} \text{ for}$$

$$k \square \{1, 2, \ldots C-1\}$$ Eq. 7

The distance to the next higher score can be measured by the difference between the actual percentage of cells ICP(k+1) to the required percentage of cells to pass the threshold T(k+1) for the next higher score S(k+1). Intuitively, this provides a measure of how close it is to pass the threshold to the next higher score. If 0% of the cells passed the threshold for the next higher score, the actual score should be close to the border to the next lower score (e.g. 1.5 if the discrete score is 2). If the actual percentage of cells is very close to the threshold for the next higher score, the actual score should be close to the border to the next higher score (e.g. 2.49 if the next higher discrete score is 3). The calculation of the distance to next higher score using a linear mapping and a linear normalization to the maximum range based on the outlined intuition is shown in Eq. 8.

$$\text{Distance}(k) = (S(k+1) - S(k-1)) \times \frac{ICP(k+1)}{T(k+1)} \text{ for}$$

$$k \square \{1, 2, \ldots C-2\}$$ Eq. 8

Often the first discrete score S(0), typically chosen to be 0, is the absolute lowest score and the continuous scoring scheme should also start with this first discrete score S(0). The anchor and the mapping intervals for the different criteria may need to be modified for the first discrete score S(0). Using a confidence in the actual score criteria, this can be thought of as always having 100% confidence into the first score S(0). Consequently, such criteria could be implemented as a constant using the maximum of its mapping interval. Using a distance to the next higher score criteria as outlined in Eq. 8, the mapping could be changed to the interval from S(0) to the half point between S(0) and S(1) as shown in Eq. 9. This has the advantage that any percentage of cells that goes towards passing the threshold for the next higher score S(1) are reflected in the continuous score.

$$\text{Distance}(0) = (S(1) - S(0)) \times \frac{ICP(1)}{T(1)}$$ Eq. 9

The mapping intervals for the different criteria may need to be modified for the last discrete score S(C−1) as well. Using a distance to the next higher score criteria, this criteria should not apply to the last discrete score as there is no next higher score.

The continuous scoring can then be calculated as shown in Eq. 10.

$$\text{Score}_{continuous} = \text{Score}_{discreet} + \text{Distance}(0)$$

for $\text{Score}_{discreet} = S(0)$ $$\text{Score}_{continuous} = \text{Score}_{discreet} - 0.5 \times (S(k) - S(k-1)) + \max(\text{Confidence}(k), \text{Distance}(k))$$

with $k = \arg_c \max\{S(c) \times [ICP(c) \geq T(c)]; c \square \{1, 2, \ldots C-2\}\}$
for $\text{Score}_{discreet} \square S(1), S(2), \ldots S(C-2)$ $$\text{Score}_{continuous} = \text{Score}_{discreet} - 0.5 \times (S(C-1) - S(C-2)) + \text{Confidence}(C-1)$$ Eq. 10:

for $\text{Score}_{discreet} = S(C-1)$

Figure 1B:
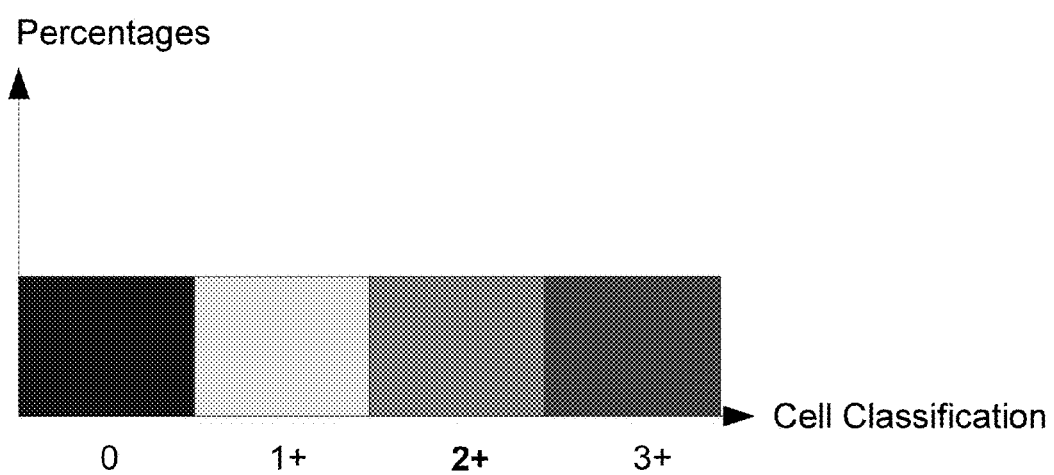
FIG. 1B shows the percentages of cells for the ranked cell classification categories.
Figure 1C:
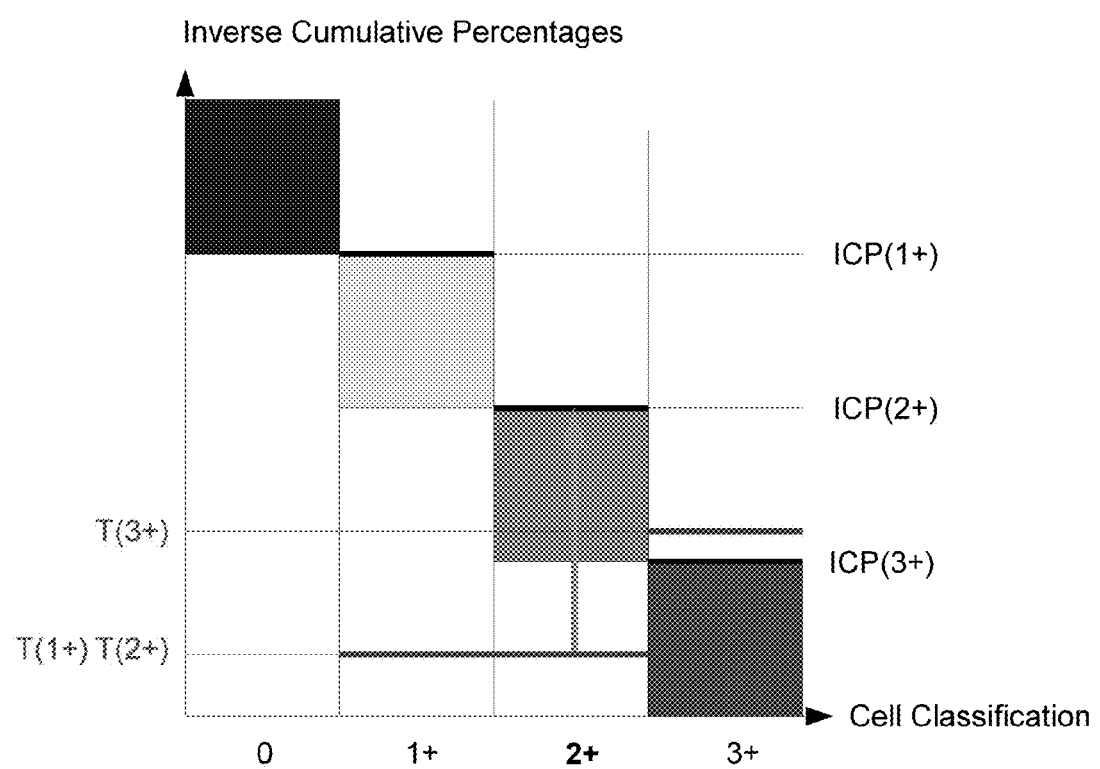
FIG. 1C shows the inverse cumulative percentages for the ranked cell classification categories
Figure 2A:
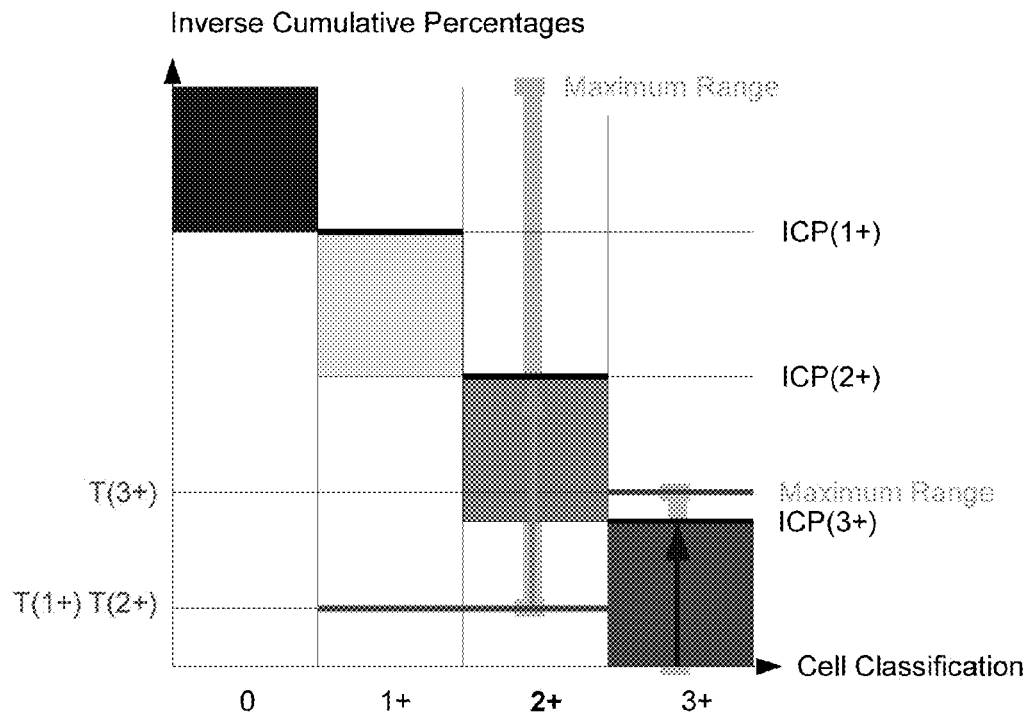
FIG. 2A shows the inverse cumulative percentages for the ranked cell classification categories in accordance with a continuous scoring scheme.
Figure 2B:
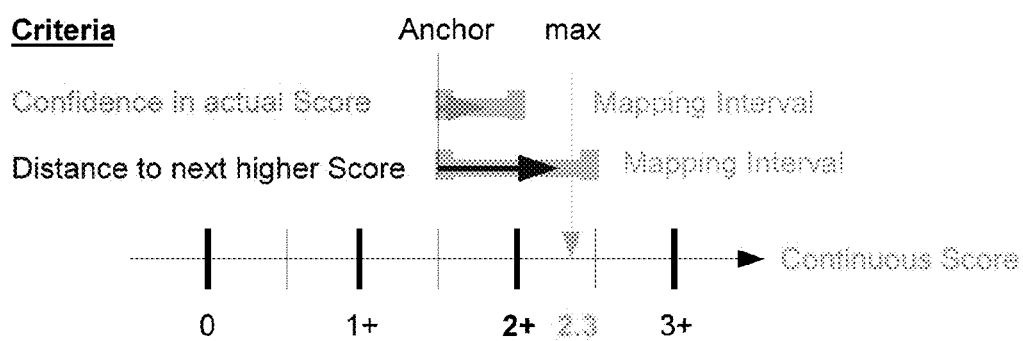
FIG. 2B illustrates how the normalized measurements of the criteria are mapped to provide a continuous score

The discrete scoring schemes that provide 0, 1+, 2+ and 3+ scores and that are based on a cell classification into 0, 1+, 2+ and 3+, like the IHC HER2 scoring scheme, can be extended to a continuous scoring scheme by applying this method, shown in Eq. 11, Eq. 12, Eq. 13 and Eq. 14.

$$\text{Confidence}(k) = 0.5 \times \frac{ICP(k) - T(k)}{100\% - T(k)} \text{ for}$$ Eq. 11

$$k \square \{1+, 2+, 3+\}$$

$$\text{Distance}(k) = 1.0 \times \frac{ICP(k+1)}{T(k+1)} \text{ for } k \square \{1+, 2+\}$$ Eq. 12

$$\text{Distance}(0) = 0.5 \times \frac{ICP(1+)}{T(1+)}$$ Eq. 13

$$\text{Score}_{continuous} = \text{Score}_{discreet} + \text{Distance}(0) \text{ for}$$
$$\text{Score}_{discreet} = 0$$

$$\text{Score}_{continuous} = \text{Score}_{discreet} - 0.5 + \max(\text{Confidence}(k), \text{Distance}(k)) \text{ for } \text{Score}_{discreet} \square 1+, 2+$$

with $k = \arg_c \max\{S(c) \times [ICP(c) \geq T(c)]; c \square \{1+, 2+, 3+\}\}$ $$\text{Score}_{continuous} = \text{Score}_{discreet} - 0.5 + \text{Confidence}(3+) \text{ for}$$
$$\text{Score}_{discreet} = S(3+)$$ Eq. 14:

FIGS. 2(A-B) illustrate the extension of the discrete IHC HER2 scoring scheme to a continuous scoring scheme. FIG. 2A shows the inverse cumulative percentages for the ranked cell classification categories as in FIG. 1. The measurements and the corresponding maximum ranges for the normalization for the two criteria, the confidence in the actual score and the distance to the next higher score, are illustrated for the cell classification category 2+ that determined the discrete score of 2+. The difference between the inverse cumulative percentage of cells ICP(2+) and the threshold T(2+) associated with the actual score, shown as a green arrow, is measured for the confidence into the actual score. The corresponding maximum range, shown as a gray bar, goes from the threshold T(2+) to 100%. The inverse cumulative percentage of cells ICP(3+) associated to the next higher score, shown as a blue arrow, is measured for the distance to the next higher score. The corresponding maximum range, shown as a gray bar, goes from 0% to the threshold T(3+). FIG. 2B illustrates how the normalized measurements of the criteria are mapped to provide a continuous score. The anchor for the criteria corresponding to the actual discrete score of 2+ is 1.5. The confidence in the actual score criteria is mapped from 1.5 to 2.0. The distance to the next higher score is mapped from 1.5 to 2.0. The normalized measurements from the two criteria taken from FIG. 2A are mapped linearly to the mapping intervals. The maximum of the two criteria is calculated to determine the continuous score of 2.3.

FIG. 3 shows a few different cell distributions with the corresponding continuous HER2 scores. P(0), P(1+), P(2+) and P(3+) are the percentages of cells per cell classification category. Note that rounding of the continuous HER2 score will yield the discrete HER2 score.

REFERENCES

[1] American Society of Clinical Oncology-College of American Pathologists Guideline Recommendations for Human Epidermal Growth Factor Receptor 2 Testing in Breast Cancer; Antonio C. Wolff, M. Elizabeth H. Hammond, Jared N. Schwartz, Karen Hagerty, D. Craig Allred, Richard Cote, Mitchell Dowsett, Patrick L. Fitzgibbons, Steven Gutman, Wedad Hanna, Patricia Keegan, Amy Langer, Lisa M. McShane, Soonmyung Paik, Mark D. Pegram, Edith A. Perez, Michael F. Press, Anthony Rhodes, Catharine Sturgeon, Sheila Taube, Raymond Tubbs, Gail H. Vance, Marc van de Vijver, Thomas Wheeler, Judy Yost, and Daniel F. Hayes; Journal of Clinical Oncology, Vol 25, No 1 (January 1), 2007: pp. 118-145

What is claimed is:

1. A method for the assessment of biomarker expressions in tissue analysis, comprising:
   detecting a plurality of cells within a digital image of a tissue section using a computerized system programmed for digital analysis of microscopy images;
   detecting one or more features for each cell of the plurality of cells, said features including staining associated with a cell membrane;
   classifying each of said detected cells into one of a plurality of cell classifications based on said detected features;
   counting an amount of detected cells for each of said cell classifications;
   calculating the percentage of the plurality of cells for each cell classification;
   determining a discrete score for the digital image, wherein said discrete score is based on the percentage of the plurality of cells for each cell classification and a threshold value associated with each of the cell classifications;
   the method further comprising:
   applying an algorithm configured to calculate a continuous score; wherein said continuous score comprises a combination of the discrete score for the digital image and one of: a distance to a next highest discrete score, a confidence of the discrete score, or a combination thereof; and
   representing the continuous score corresponding to the digital image.

2. The method according to claim 1, wherein said cell classifications are based on one or multiple cell features.

3. The method according to claim 2, wherein said cell features include a characterization of the cell morphology.

4. The method according to claim 2, wherein said cell features include a characterization of the cell neighborhood.

5. The method according to claim 2, wherein said cell features include a characterization of the expression of one or multiple biomarkers.

6. The method according to claim 1, wherein said cell classification includes any mapping of one or multiple cell features to discrete ranked categories.

7. The method according to claim 1, wherein said cell classification includes cell classifiers provided by machine-learning techniques.

8. The method according to claim 1, wherein said continuous scoring scheme is an extension of a discrete scoring scheme.

9. The method according to claim 8, wherein said discrete scoring scheme is based on a classification of the cells into a number of ranked categories, the cells are counted per cell classification category and a discrete ranked score is determined by applying thresholds to the percentages of cells in those cell classification categories.

10. The method according to claim 8, wherein said extension uses a formula that provides the continuous values between the discrete scores.

11. The method according to claim 10, wherein said formula is a function of different criteria.

12. The method according to claim 11, wherein said function includes the maximum function of the criteria that are mapped to corresponding continuous scoring intervals.

13. The method according to claim 12, wherein said mapping of the criteria to corresponding continuous scoring intervals is based on expressing the criteria relative to the discrete scores and using an anchor with a maximum range for the mapping.

14. The method according to claim 12, where the calculations of the wherein said criteria include a normalization of the criteria.

15. The method according to claim 11, wherein said criteria include a confidence into the actual score criteria.

16. The method according to claim 15, where the calculation of the wherein said confidence into the actual score criteria is based on the difference between the actual inverse cumulative percentage of cells and the required inverse cumulative percentage of cells to pass the threshold for the actual score.

17. The method according to claim 11, wherein said criteria include a distance to the next higher score criteria.

18. The method according to claim 17, where the calculation of the wherein said distance to the next higher score criteria is based on the difference between the actual inverse cumulative percentage of cells and the required inverse cumulative percentage of cells to pass the threshold for the next higher score.

19. The method according to claim 8, wherein said discrete scoring scheme is the IHC HER2 scoring scheme.

20. A method for the assessment of biomarker expressions in tissue analysis, comprising:
   detecting a plurality of cells within a digital image of a tissue section using a computerized system programmed for digital analysis of microscopy images;
   characterizing the cells based on one or more cell classifications, said cell classifications including at least staining of a cell membrane of each detected cell of the plurality of cells;
   for each of the cell classifications, counting the amount of cells characterized as meeting the cell classification;
   calculating an inverse cumulative percentage for each cell classification;
   defining thresholds associated with the cell classifications;
   assigning a discrete score associated with biomarker expression of the digital image;
   determining a confidence of the discrete score;
   determining a distance to the next higher discrete score;
   creating a continuous score associated with the digital image, wherein the continuous score comprises a combination of the discrete score for associated with biomarker expression of the digital image and one of: the distance to the next highest discrete score, the confidence of the discrete score, or a combination thereof; and mapping the continuous score about the digital image.

* * * * *